US006586263B2

(12) United States Patent  
Muradian et al.

(10) Patent No.: US 6,586,263 B2  
(45) Date of Patent: Jul. 1, 2003

(54) CORRECTION OF OVERLAY OFFSET BETWEEN INSPECTION LAYERS IN INTEGRATED CIRCUITS

(75) Inventors: David Muradian, Yerevan (AM); Arman Sagatelian, Sunnyvale, CA (US)

(73) Assignee: Neuristics Physics Laboratory, Inc., San Jose, CA (US)

( * ) Notice: Subject to any disclaimer, the term of this patent is extended or adjusted under 35 U.S.C. 154(b) by 55 days.

(21) Appl. No.: 09/747,497

(22) Filed: Dec. 22, 2000

(65) Prior Publication Data

US 2002/0102747 A1 Aug. 1, 2002

Related U.S. Application Data

(60) Provisional application No. 60/233,343, filed on Sep. 18, 2000.

(51) Int. Cl.[7] .................. H01L 21/66; G06F 19/00
(52) U.S. Cl. .................................... 438/14; 702/83
(58) Field of Search ............... 438/5, 7, 14, 16, 438/401; 700/121; 702/81, 83, 84

(56) References Cited

U.S. PATENT DOCUMENTS

| | | | | |
|---|---|---|---|---|
| 5,267,017 A | | 11/1993 | Uritsky et al. ............... 356/615 |
| 5,777,901 A | | 7/1998 | Berezin et al. ............... 716/19 |
| 5,828,778 A | * | 10/1998 | Hagi et al. .................. 382/145 |
| 5,870,187 A | | 2/1999 | Uritsky et al. ............ 356/237.2 |
| 5,991,699 A | * | 11/1999 | Kulkami et al. ............... 438/10 |
| 6,035,244 A | | 3/2000 | Chen et al. .................. 700/110 |
| 6,202,037 B1 | * | 3/2001 | Hattori et al. ............... 700/109 |
| 6,423,555 B1 | * | 7/2002 | Babcock ....................... 257/48 |

FOREIGN PATENT DOCUMENTS

| | | | | |
|---|---|---|---|---|
| EP | 0 641 020 A2 A3 | | 3/1995 | ......... H01L/21/66 |
| WO | WO 01/98835 | * | 12/2001 | ............. G03F/7/20 |

OTHER PUBLICATIONS

Segal et al. "Determining Redundancy Requirements for Memory Arrays with Critical Area Analysis" IEEE Workshop on Memory Technology, Design, and Testing, 1999.

* cited by examiner

Primary Examiner—Evan Pert  
(74) Attorney, Agent, or Firm—Sierra Patent Group, Ltd.

(57) ABSTRACT

A first method for determining the offset between the origins of the coordinate systems used for inspection of at least two different defect inspections of a wafer with integrated circuits disposed on it, comprises creating a database containing location data for defects disposed on at least two inspection layers of an integrated circuit wafer; defining maximum offsets for interlayer defects; defining minimum spacings for intralayer defects; for all defects having spacings larger than the minimum spacings searching the database for interlayer defect pairs having offsets smaller than the maximum offsets; calculating an actual offset for each interlayer defect pair; determining whether the actual offsets are randomly distributed; identifying dense zones for the actual offsets if they are not randomly distributed; and developing an estimate of the offset between the origins of the at least two layers and a confidence value for the estimate for said actual offsets. A second method comprises identifying from the database at least one die having a number of defects nd wherein $0 \leq nd \leq k$ where k is an integer less than or equal to 5, identifying all interlayer defect pairs on the at least one die, and calculating an actual offset for each interlayer defect pair in place of defining maximum offsets for interlayer defects and defining minimum spacings for intralayer defects.

15 Claims, 8 Drawing Sheets

CORRECTION OF OVERLAY OFFSET BETWEEN INSPECTION LAYERS IN INTEGRATED CIRCUITS

CLAIM OF PRIORITY

This application claims priority from U.S. Provisional Application No. 60/233,343, filed Sep. 18, 2000, entitled "CORRECTION OF OVERLAY OFFSET BETWEEN INSPECTION LAYERS IN INTEGRATED CIRCUITS."

FIELD OF THE INVENTION

The present invention relates to the manufacturing of integrated circuits. More specifically, the present invention relates to identifying defects in integrated circuits being manufactured on a wafer.

PRIOR ART

Integrated circuits are commonly manufactured in batches on wafers. Multiple integrated circuits are manufactured on a single silicon wafer during the manufacturing process. Referring now to FIG. 1, there is shown a silicon wafer having a plurality of integrated circuits disposed thereon referenced by numbers 12, 14, 16, and 18.

During the manufacturing process, multiple masking processes are performed on the semiconductor wafer. Each masking process defines where features on various layers that make up the integrated circuit are to be positioned. For example, a layer of polycrystalline silicon may be deposited on a wafer. Then photosensitive resist is coated on the wafer and selectively exposed to light so that after developing the resist, the remaining resist forms a pattern. This pattern is then transferred to the polysilicon during an etch step so that after the remaining resist is removed, the polycrystalline silicon forms a pattern defined by the selective light exposure.

This masking and etching process sequence is repeatedly carried out on each wafer to create the intricate interconnected patterns of semiconductors, insulators, and metals needed to create the desired integrated circuit (IC).

The process described above is carried out to produce a plurality of IC's on a wafer as shown in FIG. 1. For example, a single silicon wafer may be the basis for tens to thousands of IC's. The ability to manufacture a plurality of IC's on a single silicon wafer reduces the overall cost of production, thereby passing these cost savings onto the consumer in the form of inexpensive IC's.

With advancements in technology, IC's have become very small and very complex. With each generation, IC features become smaller because of advancements in the manufacturing process described above. However, with these advancements it has become more difficult to detect defects.

As part of the manufacturing process, in an effort to reduce the number of defective IC dice, it is common to inspect all of, or a sample of, the dice on a sampling of the wafers being produced. The inspection may be an optical inspection with very sensitive optical instruments capable of detecting defects of the size of a minimum feature of the IC or might be an electrical test that, in the case of memories, is capable of locating the position of an electrical defect to within the area of one small cell. The artifacts that are detected serve to guide the engineers to where defects, which may lead to yield loss, occur.

Referring now to FIG. 1 there is shown a wafer having four dice labeled 12, 14, 16, and 18. The labeled dice illustrate how a wafer may be inspected during manufacturing. For example, each of these dice, either picked randomly or according to some reason, would be inspected for defects.

Referring now to FIG. 2, there is shown a hypothetical collection defects that might be observed in an inspection report generated from inspecting the dice shown in FIG. 1. A line defect 24 is illustrated on die in FIG. 2. A line defect may be caused by a scratch on the wafer. Also shown on dice 12, 14, and 16 in FIG. 2, are a plurality of "point" defects 22, 26, 28, 34, 36, and 38. Also illustrated on die 16 in FIG. 2 is a large continuous defect 30 and a cluster of point defects 32 on die 18.

Referring now to prior art FIG. 3, there are shown defects 42, 44, 45, 46, 48, 52, 54, 58, 60, 62, and 68 that might be observed on another inspection report of the same dice later in the manufacturing process. The outline of the die is shown for illustrative purposes only in FIGS. 2 and 3 and would not be generally available in a standard defect inspection report.

Defects that occur on one layer may propagate through and also appear on subsequent levels during the manufacturing and inspection process. For example, a large contaminating particle that remains after cleaning of the polysilicon layer, might penetrate through the intervening dielectric layer and be seen on the metal contact layer. It is important to identify these propagating defects so that the cause of the defects can be correctly assigned.

After locating the defects, an overlay report may be generated in which the defects from the inspections of the successive layers are displayed together with the intention of identifying those defects that are reported to be at the same location on inspection of successive layers. However, experience has shown that there is an offset in the reported origin of the inspections between layers.

Referring now to FIG. 4, there is shown an exemplary overlay report as would be created after performing at least two inspections. As shown in FIG. 4, an offset in the origins of the coordinate systems used to report the location of the defects may cause the defects from one layer to be incorrectly positioned with respect to those defects of a second layer. This offset has been a recurring problem in the manufacture of integrated circuits and, as the size of the integrated circuits features are reduced and the number of dice on a wafer increases, there is a growing need to correct this problem.

Thus, when an overlay inspection report is generated as shown in FIG. 4, propagating defects may not be identified. As shown in FIG. 4, only individual point defects from the defect clusters 32 and 62 would be selected. An attempt to identify correlated defects as those lying within some critical distance of each other would mistakenly select the pair of defects 48, both of which come from the second inspection. A more sophisticated correlation algorithm based on defects from successive inspections that lie within a critical distance would misidentify defects 45 and 26 as being correlated when in fact they are not.

Therefore, there is a need for a procedure for automatically detecting the origin offset between the inspections and correcting the offset in the overlay report so that the correlated defects that propagate between layers can be identified correctly. The present invention provides a method and apparatus for correcting these.

It is an object of the present invention to provide methods for correcting the offset between origins of coordinate systems for layers so that during the manufacturing process correlating defects are correctly identified. It is a further object of the present invention to provide a method that can be implemented during the manufacturing process so that defective dice can be disposed of properly.

SUMMARY OF THE INVENTION

The present invention provides a method for detecting correlated defects during the manufacture of integrated circuits. In one embodiment, the method of the present invention searches for pairs of defects lying within a given distance of each other from differing layers. The distances or spacings between pairs are calculated and a statistical algorithm is performed to determine if the defect pair spacings are distributed randomly. If there exists a subset of defect pairs is isolated and used to calculate the offset of the origins of the coordinates of each of the layers.

In a second embodiment, the method of the present invention automatically searches for defect pairs between layers over a space equal to the size of the die being inspected using a k-restricted sampling where k is restricted to a small integer, typically k ranges from 0 to 3. The use of k-restricted sampling ensures that problems caused by clustered defects are avoided. Once the defect pairs are selected by either of the methods described above, the defect pairs are tested to determine whether the spacing between the members of the pairs are distributed randomly. If the distribution is not random, the non-random subset of defect pairs is isolated, then the isolated subset of defect pairs is used to calculated the offset of the origins for the two layers.

The invention further relates to machine readable media on which are stored embodiments of the present invention. It is contemplated that any media suitable for retrieving instructions is within the scope of the present invention. By way of example, such media may take the form of magnetic, optical, or semiconductor media. The invention also relates to data structures that contain embodiments of the present invention, and to the transmission of data structures containing embodiments of the present invention.

DETAILED DESCRIPTION OF THE INVENTION

Those of ordinary skill in the art will realize that the following description of the present invention is illustrative only and not in any way limiting. Other embodiments of the invention will readily suggest themselves to such skilled persons.

In describing the present invention it is assumed that a wafer has been selected for which in-line inspection of data is available after the operations on two or more layers. In these descriptions, the problem of finding the offsets in the origins between the inspection data on two of the layers is described. It will be obvious that this operation can be readily and repeatedly applied on wafers having two or more layers. Additionally, the method of the present invention can be applied to wafers having more than two sets of inspection data.

Still further, the defect coordinates and the distance between the related defects are described in Cartesian coordinates. However, it will be obvious to one having ordinary skill in the art that the distance between related defects could be described in polar coordinates or may be described using other coordinate systems. The Cartesian coordinate system is typically used by the machines utilized to perform the inspection process. Therefore the present invention will be described in Cartesian coordinates as it will be the most convenient system to utilize.

Figure 7:
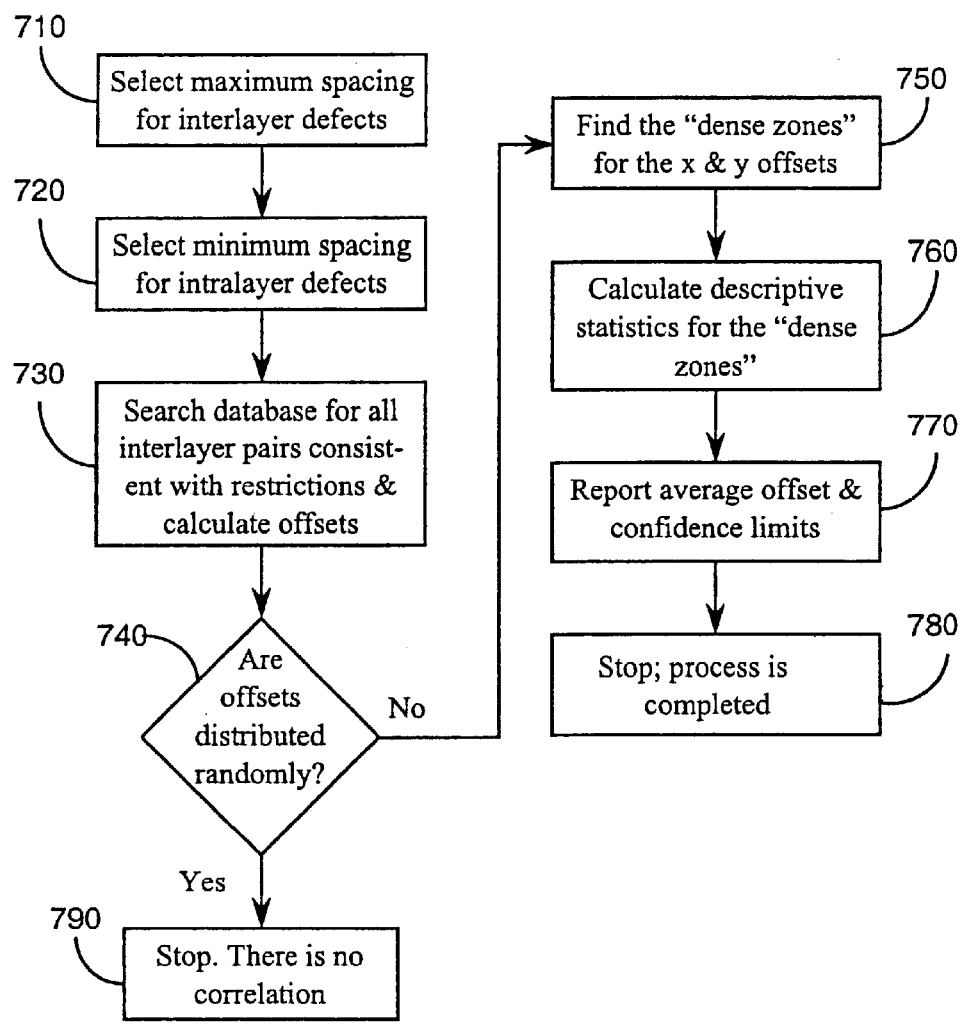
FIG. 7 is a function flow diagram illustrating the implementation of one method of the present invention.

Two separate embodiments of the present invention are separately described herein. Referring now to FIG. 7, there is shown a functional flow diagram depicting a first method of the present invention.

At BOX 710, the method of the present invention begins with the setting of maximum X and Y values (X max and Y max), e.g., the maximum allowed spacing between defects that propagate between layers during the manufacturing process. The values chosen by the user for X max and Y max may vary depending upon the equipment utilized during the inspection process. The operator having knowledge of the equipment will chose appropriate values for X max and Y max. For example, the operator may know from experience that the spacing between a pair of defects is usually less than 60 micrometers.

At BOX 720, the minimum spacing allowed for intralayer defects X min and Y min are established. The values for defects X min and Y min are dependent upon the scale of technology being utilized in the manufacturing process. In the case of a technology with the minimum feature size of 0.5 micrometers, defects on the same inspection layer spaced closer than 10 micrometers might be considered to result from clustering.

In use, defects that are disposed closer together than the pre-set X min and Y min values on the same inspection layer are excluded from the origin offset calculations. The minimum values may be selected by the user or they can be selected automatically by using the following formulas:

$X \text{ min} > 2 * X \text{ max}$ $Y \text{ min} > 2 * Y \text{ max}$

The limits for X min and Y min are established to avoid confusion that may occur when there are two or more defects on one layer that can be overlaid on another defect that will be observed on a subsequent layer.

At BOX 730, a database is searched for all interlayer defect pairs consistent with the restrictions selected previously at BOX 710 and BOX 720. The process of BOX 730 may be performed after at least two inspections have been performed on the wafer. After locating all defect pairs that satisfy the restrictions previously selected (X max, Y max, X min, Y min), the distances or spacings, $\Delta X$ and $\Delta Y$, in the coordinates of these defect pairs are calculated and saved for later use.

At Diamond 740 it is determined whether the spacings between defects calculated in BOX 730 are distributed randomly with some selected probability. For example, the distribution could be tested to determine if the probability of the observed distribution occurring as a result of random processes is less than 1%. There are a number of methods known to those skilled in the art of performing statistical calculations that may be applied to achieve the desired results. See for example, Maurice G. Kendell and Alan Stuart, "The Advanced Theory of Statistics", Vol. 2 Inference and Relationship, Hafner Publishing Co., New York (1967).

If it is determined that the distribution could have occurred randomly, then the process proceeds to BOX 790 where the process stops. Alternatively, if it is determined that the distribution could not have occurred randomly, then the process proceeds to BOX 750.

Figure 5:
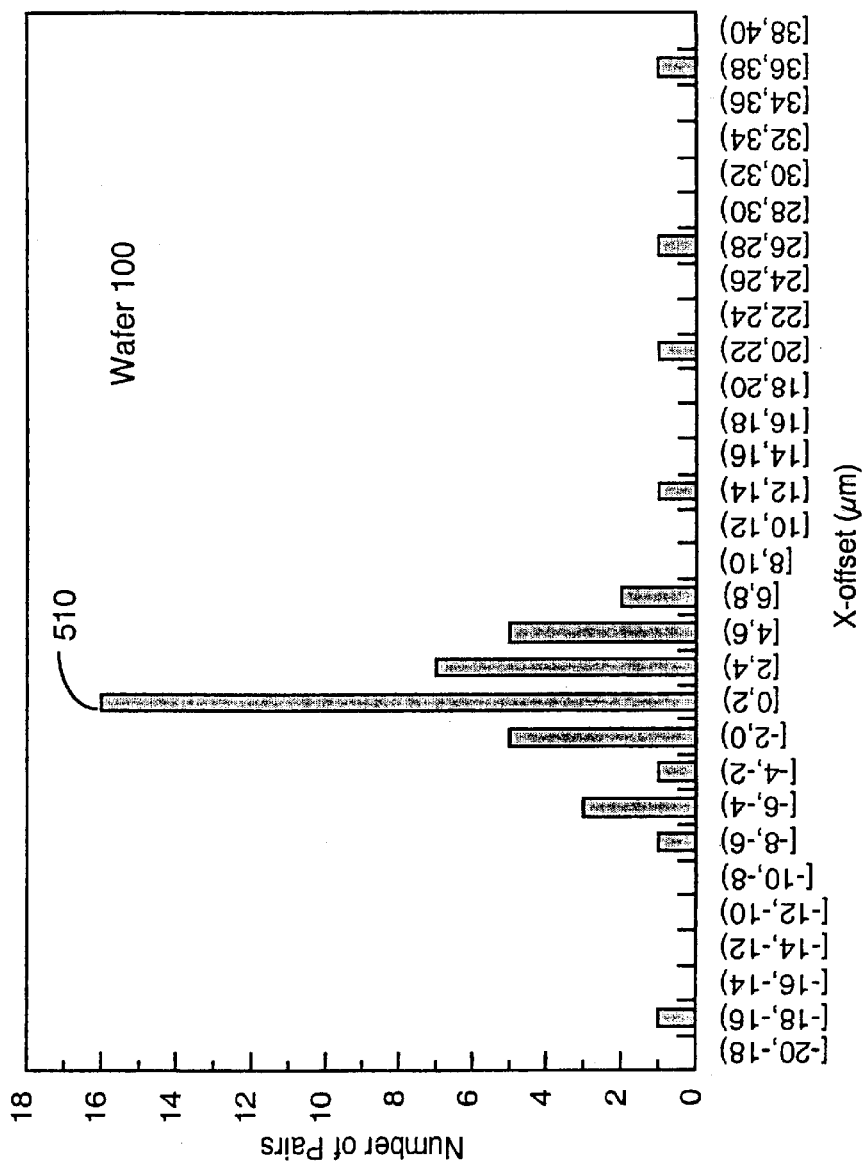
FIG. 5 is an illustration of the distributed offsets in the x-direction observed between defect pairs observed on two layers.
Figure 6:
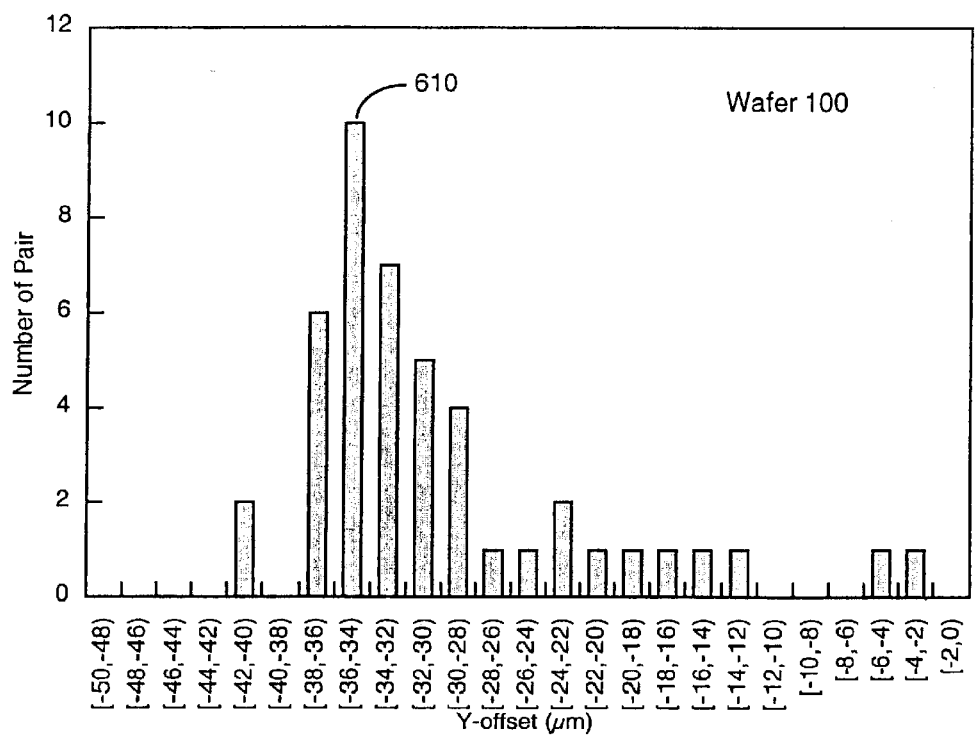
FIG. 6 is an illustration of the distributed offsets in the y-direction observed between defect pairs observed on two layers.

At BOX 750 the "dense zones" for the coordinate differences are determined as a result of the process of BOX 730. By "dense zones" is meant a region on each of the coordinate offset axes where there is a relatively high density of defect pairs found. In FIG. 5 it is seen that there is a relatively high density of defect pairs occurring in the range $-8$ μm to $+8$ μm. In FIG. 6 a similar cluster of defect pairs is observed between $-42$ μm and $-28$ μm.

The histograms of distances between defect pairs seen on a wafer for the x-coordinate and y-coordinate are shown in FIGS. 5 and 6, respectively. Referring now to FIG. 5, there is shown an exemplary histogram that may be generated during an inspection process undertaken on wafer 100. As shown in FIG. 5, there is a peak value 510 in the distribution of differences in the region between 0 and $+2$ μm.

Referring now to FIG. 6, there is shown an exemplary histogram that may be generated during an inspection process undertaken on wafer 100. As shown in FIG. 6, there is a peak value 610 in the distribution of differences in the region between $-36$ μm and $-34$ μm.

Each of the dense zones in FIGS. 5 and 6 have roughly a Gaussian distribution because the central limit theorem assures that the scatter in a number of observations that arise from several causes will tend to approximately a Gaussian distribution as the number of observations increases.

Referring now to FIG. 7, specifically BOX 750, there are a number of possible heuristic algorithms for determining the "dense zones." For example, the range of coordinate differences, X max and Y max, could each be divided into a number of equal segments, e.g. 10 segments. The number of points falling into each segment are counted and the segments containing the greatest number of points falling within that segment for x-coordinate differences and for y-coordinate differences are selected as the most likely location of the dense zone.

Alternatively, the program can search for the set of intervals for which the count of observations is maximal using the following equations:

$$(\Delta X\text{upper} - \Delta X\text{lower}) < X \text{ max}/10;$$

and $$(\Delta Y\text{upper} - \Delta Y\text{lower}) < Y \text{ max}/10.$$

In the equations given above, $\Delta X$upper is the upper value and $\Delta X$lower is the lower value, respectively, for a segment of an ordered array of the $\Delta X$ values. $\Delta Y$upper and $\Delta Y$lower, are respectively the upper and lower values for a segment of an ordered array of $\Delta Y$ values. The two examples described above are merely exemplary in nature and should not be considered limiting. As one who is skilled in the art will appreciate, there are many methods that may be utilized to determine the "dense zones"; each of which can be utilized with the invention described herein.

At BOX 760, after the dense zones have been identified, the standard descriptive statistics, i.e., the average, standard deviation, the upper and lower confidence limits, and an interval size for the confidence interval are calculated. The averages are taken as the best estimate of the offsets of the origins between the two layers and the confidence limits indicate the range within which the "true" offset of the origins is expected to lie. In this embodiment, the average is utilized as the estimate of the "true" offset of the origins both because of its intuitive appeal and because of its computational simplicity. It may be obvious to those ordinarily skilled in the art that other metrics could be utilized to define the "true" offset of the origins. For example, the median may be utilized as the estimate of the offset of the origins rather than the average. Similarly, one could use a maximum likelihood approach to estimate the "true" offset of the origins from the observations in the dense zones.

At BOX 770 the calculated offset and confidence limits are reported to the user so that they may be utilized to determine propagating dice and other defects on wafer 100.

At BOX 780, the process ends and is reset for use on the next wafer being processed.

Figure 8:
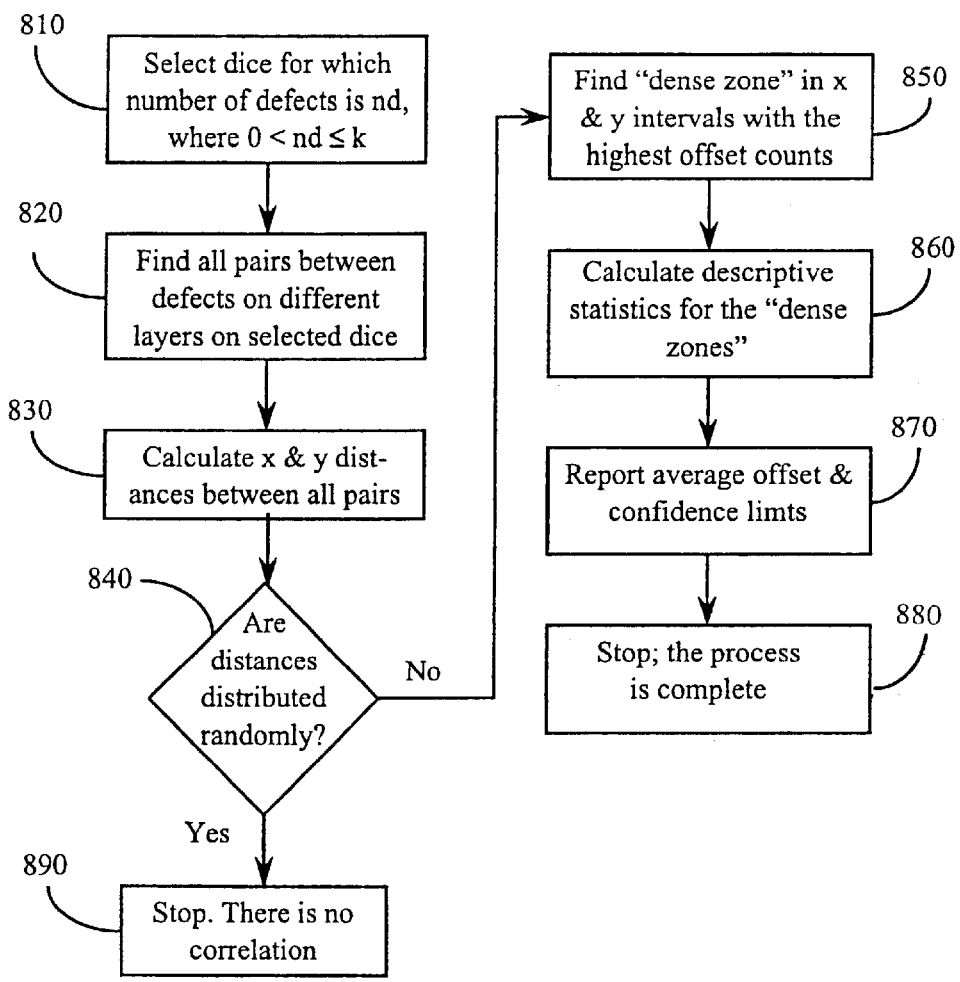
FIG. 8 is a functional flow diagram illustrating a second automated method of the present invention.

Referring now to FIG. 8, there is shown a functional flow diagram depicting a second automated method according to the present invention. With reference to FIG. 8, an automated process for determining offsets between origins of the layers is described. The process is referred to herein as k-restricted sampling. The k-restricted sampling is applied to avoid the confusion that occurs when a defect is observed on one layer that can be overlaid on either of two different defects on another layer. The k-restricted sampling of the present invention should not be confused with the k-statistics of R. A. Fisher.

Figure 1:
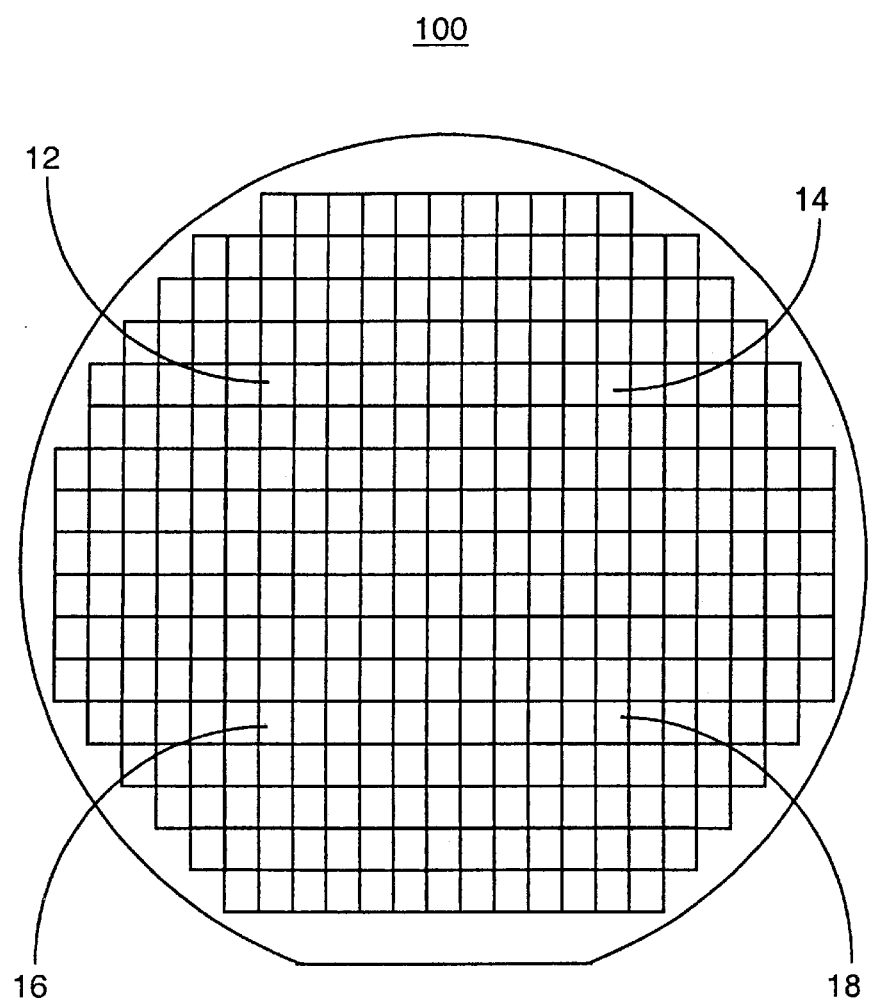
FIG. 1 is an illustration of a prior art wafer showing the division into an array of dice.
Figure 2:
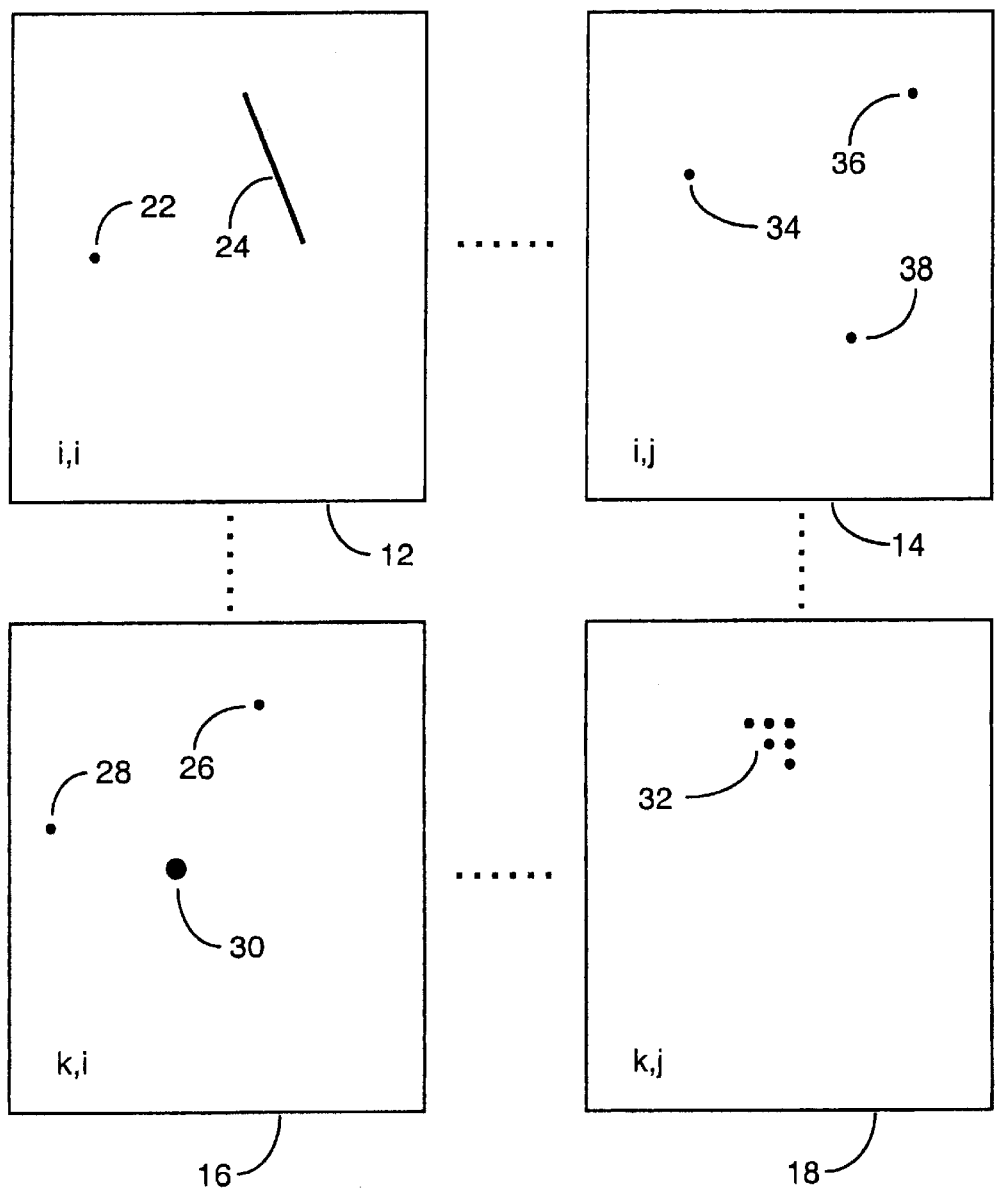
FIG. 2 is an exemplary illustration of defects that may be detected during an inspection process.
Figure 3:
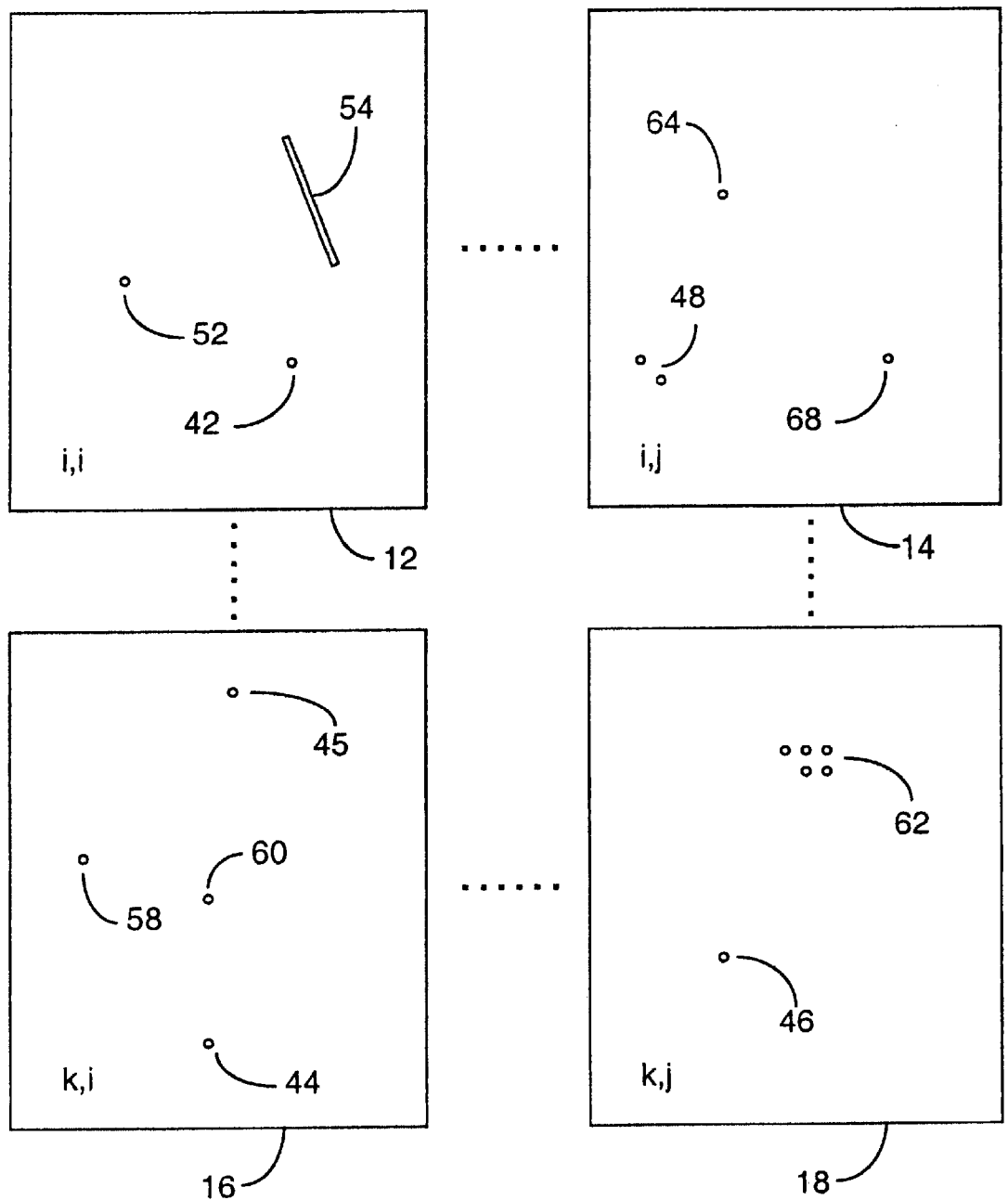
FIG. 3 is an illustration of defects that may be detected after a second layer has been processed on a wafer.
Figure 4:
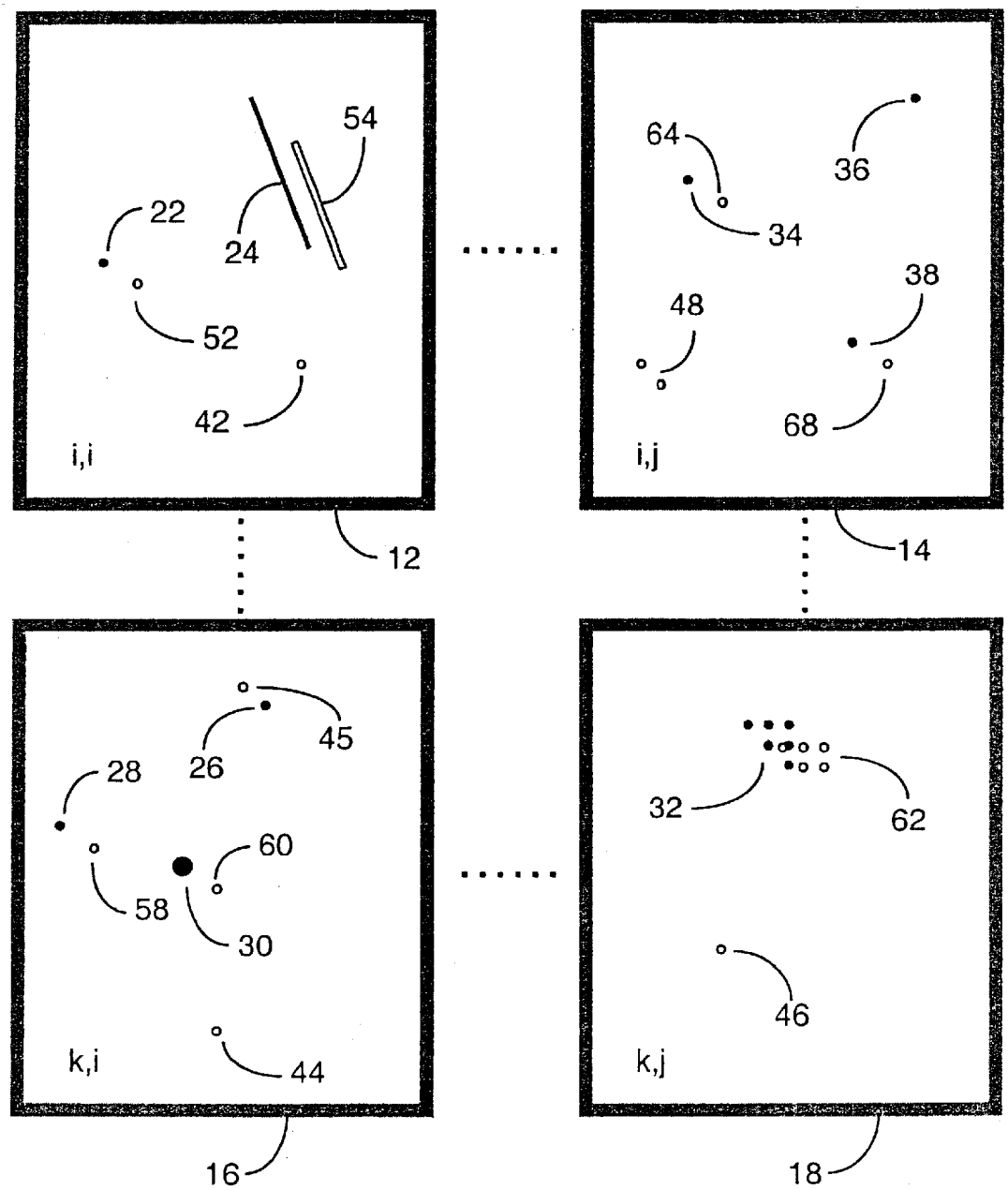
FIG. 4 is an illustration of an overlay report that may be created after at least two inspections showing defects as identified on different layers.

For example, the defects in the cluster 32 and the defects in the cluster 62 seen in FIG. 4 have the potential to confuse a calculation of offset of the origins of the layers. In the method described above, the restriction on the minimum spacing between defects on the same layer is used to remove clusters 32 and 62 from the offset calculation. In the embodiment disclosed with reference to FIG. 7, the restriction on the minimum spacing between defects on the same layer is used to remove the clustered defects 32 and 62 from the calculation. In an automatic embodiment of the present invention, the operator intervention of choosing X max and Y max is eliminated.

Referring now to FIG. 8, at BOX 810, the values for X max and Y max are taken to be the dimensions of the die under study. These values are extracted from the database. The problem of confusion of multiple defects is avoided by restricting the dice on which the calculations are carried out to those for which the number of defects, nd, satisfies the constraint $0 \leq nd \leq k$ where k is a small integer. Typically k is less than or equal to 3. If k is equal to 1, then the chance of confusion is zero. If, for example, k is set equal to 2, then assuming that for a die nd=2, and that none of the defects are propagating, 2 or 4 random pairs of $\Delta X$ and $\Delta Y$ are introduced into the list of pair differences, depending upon whether there are two defects on both layers or on only one of the two layers. If one of the defects is propagating, there will be one matched pair and 1 or 3 random pairs introduced into the list of different pairs. If there are two propagating pairs, two matched pairs and no random pairs will be entered onto the list of different pairs.

This reasoning can be carried out on the k=n, but it becomes clear that the number of possibilities of random pairs increases faster than the possibilities of matched pairs so that the "noise" can overwhelm the "signal". For this reason, the value of k is chosen to be ≦3, and is typically chosen to be 1 for a first try at determining the offset.

At BOX 820, all defect pairs are identified on selected dice on two different layers disposed on the wafer.

At BOX 830, ΔX and ΔY of the pairs are determined according the process, described above.

At Diamond 840, the newly determined ΔX and ΔY pairs are tested to determine if they are distributed randomly. If the pairs are randomly distributed then the process advances to BOX 890 and the process stops. Alternatively, if it is determined that the pairs are not randomly distributed, there is an observed propagation of defects and the process advances to BOX 850.

At BOX 850, the dense zones for both X values and Y values are calculated as described above.

At BOX 860, after locating the dense zones, the process proceeds to calculate an estimate of offset of the origins and statistical uncertainty of the estimate as described in the process above.

At BOX 870, the offset and the statistical uncertainty are displayed to the user.

At BOX 880, the process is ended and reset for use on the next wafer being processed.

When the automatic method described above and depicted in FIG. 8 is employed, the sample size of the number of pairs for which differences are calculated will be small in cases where there are few dice with a small number of defects. This may lead to more uncertainty in the estimate of the offset.

Each of the methods described herein may be utilized independently, or alternatively may be utilized concurrently. For example, the same data may be utilized for both processes. The user can then choose the calculated offset that gives the best result or utilize the result of the automatic approach as an input for the semi-automatic approach.

While embodiments and applications of this invention have been shown and described, it would be apparent to those skilled in the art that many more modifications than mentioned above are possible without departing from the inventive concepts herein. For example, although the present invention has been described in detail regarding the utilization of specific mathematical equations, it should be understood by one skilled in the art that there are a plurality of equations that may be utilized instead of those described herein. The invention, therefore, is not to be restricted except in the spirit of the appended claims.

What is claimed is:

1. A method for determining an offset between origins of coordinate systems of at least two layers of a wafer used for inspection of at least two different defect inspections of said wafer upon which integrated circuits are disposed, the method comprising:
   creating a database containing location data for defects disposed on at least two inspection layers of an integrated circuit wafer;
   defining a maximum spacing between a pair of interlayer defects;
   defining a minimum spacing between a pair of intralayer defects;
   detecting all pairs of interlayer defects;
   determining each of said pairs of interlayer defects having a spacing that are greater than said minimum spacing and less than said maximum spacing;
   calculating an actual spacing for each pair of interlayer defects determined to have said spacing greater than said minimum spacing and less than said maximum spacing;
   determining whether said actual spacings are randomly distributed;
   identifying dense zones for said actual spacings responsive to said actual spacings not being randomly distributed; and
   developing an estimate of the offset between the origins of said at least two layers from said spacings and a confidence value for said estimate for said actual spacings.

2. The method of claim 1, wherein developing an estimate comprises:
   calculating an average of said actual spacings.

3. The method of claim 1, wherein developing an estimate comprises:
   calculating a median of said actual spacings.

4. The method of claim 1 wherein:
   defining said maximum spacing for interlayer defects comprises defining said maximum spacing for interlayer defects in x and y coordinates;
   defining said minimum spacing for interlayer defects comprises defining said minimum spacing for interlayer defects in x and y coordinates;
   calculating said actual spacing for each pair of interlayer defects comprises calculating said actual spacing for each pair of interlayer defects in x and y coordinates; and
   developing an estimate of the offset between the origins of said at least two layers in x and y coordinates.

5. The method of claim 4, wherein said actual spacing in the x coordinate is calculated by subtracting an x coordinate of a first one of a pair of interlayer defects reported from a first inspection from an x coordinate of a second one of said pair of said interlayer defects reported from a second inspection.

6. The method of claim 4, wherein said actual spacing in the y coordinate is calculated by subtracting a y coordinate of a first one of a pair of interlayer defects reported from a first inspection from a y coordinate of a second one of said pair of interlayer defects reported from a second inspection.

7. The method of claim 4, wherein said dense zones are determined by dividing the range of each coordinate spacing into a plurality of equal intervals and selecting a one of said plurality of equal intervals with the greatest count of spacings as the dense zone.

8. A method for determining the offset between origins of coordinate systems of at least two layers of a wafer used for inspection of at least two different defect inspections of said wafer upon which integrated circuits are disposed, the method comprising:
   creating a database containing location data for defects disposed on each of at least two inspection layers of said wafer;
   identifying from said database at least one die having a number of defects, nd, wherein 0<nd<k where k is an integer less than or equal to 5;
   identifying all interlayer defect pairs on said at least one die;
   calculating an actual spacing between defects in interlayer defect pair for each of interlayer defect pairs;
   determining whether actual spacings calculated for each of said interlayer defect pairs are randomly distributed;
   identifying dense zones for said actual spacings responsive to said actual spacings not being randomly distributed; and
   developing an estimate of the offset between the origins of said at least two layers from said actual spacings and a confidence value for said estimate for said actual spacings.

9. The method of claim 8 wherein k is an integer less than or equal to 3.

10. The method of claim 8, wherein developing said estimate comprises:

calculating an average of said actual offsets.

11. The method of claim 8, wherein developing said estimate comprises:

calculating a median of said actual offsets.

12. The method of claim 8 wherein:

calculating said actual spacing for each of said interlayer defect pairs comprises calculating an actual spacing for each of said interlayer defect pairs in x and y coordinates; and developing said estimate of the offset between the origins of said at least two layers in x and y coordinates.

13. The method of claim 12, wherein said actual spacing in the x coordinate is calculated by subtracting an x coordinate of a first defect in a pair of interlayer defects reported from a first inspection of a first layer from an x coordinate of a second defect in said pair of interlayer defects reported from a second inspection of a second layer.

14. The method of claim 12, wherein said actual spacing in the y direction is calculated by subtracting a y coordinate of a first defect in a pair of interlayer defects reported from first inspection of a first layer from a y coordinate of a second defect in said pair of interlayer defects reported from a second inspection of as second layer.

15. The method of claim 12, wherein said dense zones are determined by dividing the range of each coordinate spacing into a plurality of equal intervals and selecting a one of said plurality of intervals having the greatest count of offsets as the dense zone.

* * * * *